United States Patent [19]

Lentz et al.

[11] Patent Number: 4,691,050

[45] Date of Patent: Sep. 1, 1987

[54] CARBONYLATION PROCESS FOR THE PRODUCTION OF AROMATIC DICARBOXYLIC ACIDS

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 868,178

[22] Filed: May 23, 1986

Related U.S. Application Data

[63] Continuation of Ser. No. 707,286, Mar. 1, 1985, abandoned.

[51] Int. Cl.$^4$ .............................................. C07C 51/10
[52] U.S. Cl. ................... 562/406; 546/327; 548/536; 549/71
[58] Field of Search .................. 562/406; 546/327; 549/71; 548/536

[56] References Cited

U.S. PATENT DOCUMENTS 2,565,463  8/1951  Tabet ................................... 562/406
3,733,354  5/1973  Cassar ................................. 562/406

OTHER PUBLICATIONS

Falbe, "Carbon Monoxide in Organic Synthesis," pp. 118–120, (1970).
Allinger, "Organic Chemistry," pp. 265–267, (1972).

Primary Examiner—Michael L. Shippen
Attorney, Agent, or Firm—J. Frederick Thomsen; Charles R. Martin

[57] ABSTRACT

The present invention provides a process for the preparation of aromatic dicarboxylic acids by the carbonylation of aromatic diiodides. The aromatic diiodides are reacted with carbon monoxide in the presence of a soluble rhodium catalyst in a hydrocarbon acid reaction medium to prepare the aromatic dicarboxylic acids.

8 Claims, No Drawings

CARBONYLATION PROCESS FOR THE PRODUCTION OF AROMATIC DICARBOXYLIC ACIDS

This is a continuation of application Ser. No. 707,286 filed Mar. 1, 1985, now abandoned.

This invention relates to a novel carbonylation process for the production of aromatic carboxylic acids. More particularly, this invention relates to a process for the carbonylation of aromatic diiodides to form aromatic dicarboxylic acids. The aromatic diiodides are reacted with carbon monoxide in the presence of a soluble rhodium catalyst in a hydrocarbon acid reaction medium to prepare tne aromatic dicarboxylic acids.

The preparation of carboxylic acid derivatives by carbonylation of aromatic halides catalyzed by Group VIII metal compounds is well known in the art. One such process is described in U.S. Pat. No. 2,640,071 whereby carboxylic acid derivatives are obtained from aryl halides using nickel complexes as catalyst using high reaction temperatures of 250°–450° C. and pressure of 300 to 1,000 atmospheres. A typical example is the conversion of p-dichlorobenzene to dialkyl terephthalate at 345° C. and 350 atmospheres of carbon monoxide in the presence of a catalytic amount of nickel.

Another carbonylation process for preparing carboxylic acid derivatives known in the art is described in U.S. Pat. No. 3,988,358 whereby carboxylic acid esters are prepared from aryl halides by the reaction of a starting material such as bromobenzene with an alcohol such as butanol and carbon monoxide in the presence of a palladium catalyst and a tertiary amine.

It would therefore be an advance in the state of the art to provide a more simple process for carbonylation of aromatic dihalides to prepare aromatic dicarboxylic acids in excellent yields under milder reaction conditions.

In accordance with the present invention, it has now been found that aromatic diiodides can be carbonylated to the desired aromatic dicarboxylic acids by reaction with carbon monoxide in the presence of a soluble rhodium catalyst in a hydrocarbon acid reaction medium. The carbonylation reaction carbonylates substantially all of the aromatic diiodide present in the acidic reaction medium.

The aromatic diiodide employed as a starting material in the process of the present invention has the following chemical formula:

In the above Formula, R represents a carbocyclic or heterocyclic aromatic group having about 5 to about 20 atoms in the ring or rings thereof. Such R groups can be derived from, for example, toluene, benzene, naphthalene, pyridine, thiophene, pyrrole, and the like.

The R groups can also be substituted or unsubstituted. When substituted, typical substituents include the halides such as chlorine, bromine and iodine, alkyl groups having up to about 12 carbon atoms, vinyl groups, carboxylic acid groups, carboxylic ester groups, ether groups, and the like. The process provides aromatic dicarboxylic acids having high melting points which separate out and can be recovered substantially free of the soluble catalyst.

The aromatic diiodides employed in the process of the present invention can be prepared by the methods described in T. Hudlicky et al in *The Chemistry of Halides, Pseudohalides and Azids*, Supplement D, Part 2, 1142–1158, the disclosure of which is incorporated herein by reference in its entirety.

In the process of this invention, the aromatic diiodide described above is reacted in a hydrocarbon acid solvent, such as acetic acid, butyric acid, propionic acid and the like. A stronger organic or inorganic acid may also be added to the hydrocarbon acid solvent in an amount of 0 percent to 15 percent, by weight, preferably 2 percent to 7 percent. Examples of such stronger acids are hexafluorophosphoric acid, p-toluenesulfonic acid, sulfuric acid, hexafluoroarsenic acid, trifluoroacetic acid, fluoroboric acid, 3,3,3-trifluoropropionic acid, hydrofluoric acid, fluorosulfuric acid, dichloroacetic acid and the like.

The soluble homogeneous rhodium catalyst is provided to the reaction system in the soluble form such, for example, preferably as the rhodium trichloride. Because of the insolubility of the aromatic dicarboxylic acids prepared by this invention, it is desirable for the catalyst to be a soluble catalyst. A soluble catalyst will remain active and will not contaminate the insoluble aromatic dicarboxylic acid with catalyst. The catalyst may also be provided in a form which there is an in situ formation to the soluble form, such as by the use of rhodium. The catalyst is present in a concentration of at least about 0.02 millimole per mole of aromatic diiodide, preferably, about 0.2 to 2 millimole per mole.

The catalytic carbonylation reaction of the present invention is conducted in the presence of carbon monoxide, which is employed in amounts such that the total reaction pressure is in the range of atmospheric pressure to about 500 psig. Superatmospheric pressure may be advantageous when a volatile reactant is employed or when an increase in the rate of reaction is desirable. Thus, reaction pressures from 100 psig to about 500 psig (about 700 kPa to about 3500 kPa) are suitable, with pressures from 100 psig up to about 250 psig (about 700 kPa to about 1750 kPa) being preferred.

The process of the present invention can be conducted at temperatures of about 50° C. to about 150° C., preferably about 80° C. to 130° C.

The reaction is carried out at a pH of less than about 5. The reaction under such acidic conditions provides fast and efficient carbonylation of the aryl iodide.

The reaction mixture was cooled to 15° to 20° C. and filtered to remove the aromatic dicarboxylic acid. The hydrogen iodide by product as well as the hydrocarbon acid solvent system and soluble catalyst can be recycled. This improvement represents a more efficient and cost effective process in that the by product hydrogen iodide can be recycled. In this manner, this relatively expensive iodide component of the reaction system need not be supplied to the reaction process in considerable quantities on a continuous basis, as was necessary with prior art processes.

The novel process of the present invention therefore provides products which are useful as intermediates in the synthesis of polyesters (such as polyethylene terephthalate) and other useful polymeric materials in a unique and efficient manner.

The invention will be further illustrated by the following Examples although it will be understood that these Examples are included merely for purposes of illustration and are not intended to limit the scope of the invention.

EXAMPLES 1-10

The following Examples illustrate the carbonylation of 4-diiodobenzene in the presence of a soluble rhodium catalyst, a hydrocarbon acid solvent with a stronger acid and carbon monoxide to produce the corresponding terephthalic acid. The particular catalyst, and strong acid employed and reaction conditions in each example are indicated below in Table I. The catalyst was employed in a concentration of 0.10 millimole per mole of 1,4-diiodobenzene. The stronger acid was present in a concentration based on the weight percent of the acetic acid solvent present. In Examples 2 and 5 to 9 the acetic acid solvent contained about 3 percent by weight water. In Examples 1, 3, 4, 10 and 11 the acetic acid solvent contained acetic anhydride in an amount of about 3 percent by weight to ensure that the solvent contained substantially no water and was substantially dry.

In each Example, into a laboratory autoclave with a glass liner was added 9.1 millimoles (3.0 g) of 1,4-diiodobenzene, 0.2 g rhodium trichloride and 0.2 g lithium iodide, of the indicated mole percent stronger acid if added, and 100 ml of acetic acid. While carbon monoxide was fed beneath the surface of the reaction mixture at the indicated total pressure, the reaction mixture was heated to the indicated temperature and was held at that temperature for tne indicated period of time. The resulting mixture was cooled to 15° to 20° C. and filtered to remove the aryl carboxylic acid. The filtrate can then be used for recycling back to the preparation of the 1,4-diiodobenzene and recycle solvent and catalyst. The aryl carboxylic acid product was washed with water and dried.

The results of these Examples are given below in Table I.

Similar results are obtained using diiodonaphthalene, diiodopyridine, diiodothiophene, diiodopyrrole, and the like.

TABLE I

| Ex. | % Water | Strong Acid | Temperature (°C.) | Pressure (psig) | Conversion (%) | Time (hrs) |
|---|---|---|---|---|---|---|
| 1 | 0 | 0 | 150 | 100 | 54.9 | 4 |
| 2 | 3% | 0 | 150 | 200 | 76.9 | 4 |
| 3 | 0 | 0 | 150 | 200 | 61.5 | 4 |
| 4 | 0 | 0 | 120 | 500 | 12.0 | 4 |
| 5 | 3% | 10% HBF$_4$ | 150 | 100 | 38.7 | 4 |
| 6 | 3% | 10% HBF$_4$ | 150 | 200 | 81.5 | 4 |
| 7 | 3% | 10% HBF$_4$ | 120 | 200 | 45.0 | 4 |
| 8 | 3% | 10% HBF$_4$ | 120 | 100 | 11.3 | 4 |
| 9 | 3% | 5% H$_2$SO$_4$ | 150 | 200 | 36.0 | 4 |
| 10 | 0% | 5% H$_2$SO$_4$ | 150 | 200 | 12.4 | 4 |
| 11 | 0% | 5% CF$_3$COOH | 150 | 200 | 42.1 | 4 |

EXAMPLE 11

About 20.0 millimoles 1,4-diiodobenzene was placed into a laboratory autoclave with the same amount catalyst and acetic acid used in the preceding Examples. While carbon monoxide was fed beneath the surface of the reaction mixture at the indicated pressure, the reaction mixture was heated to the indicated temperature and was held at that temperature for the indicated period of time. Upon completion of reaction, the reaction mixture was worked up as described above. The results are given below in Table II.

EXAMPLE 12

Example 11 was repeated except that potassium iodide was used in place of lithium iodide. The reaction was worked up as described and the results given below in Table II.

EXAMPLE 13

Example 11 was repeated except that magnesium iodide was used in place of lithium iodide. The reaction was worked up as described and the results given below in Table II.

EXAMPLE 14

Example 11 was repeated except that 1 percent soluble palladium was used as the catalyst in place of 1 percent soluble rhodium, and 10% by weight fluoroboric acid, based on the weight of acetic acid, was added to the acetic acid and the mix was used as the solvent. The reaction mixture was heated to 150° C. for six hours. Upon completion of the reaction, the reaction mixture was worked up as described above. The results are given below in Table II.

EXAMPLE 15

Example 12 was repeated except that 0.1 gram nickel powder was used as the catalyst. The reaction was worked up as described and the results given below in Table II.

TABLE II

| Comp. Ex. | Catalyst | Temperature (°C.) | Pressure (psig) | Conversion (%) | Time (hrs) |
|---|---|---|---|---|---|
| 11 | 1% Rh | 150 | 200 | 615 | 4 |
| 12 | 1% Rh | 150 | 200 | 27.6 | 4 |
| 13 | 1% Rh | 150 | 200 | 29.5 | 4 |
| 14 | 1% Pd | 150 | 200 | 4.0 | 6 |
| 15 | Ni Powder | 120 | 200 | 2.9 | 6 |

These results clearly demonstrate that conversion of the 1,4-diiodobenzene to the corresponding organic acid with a different catalyst and reaction medium is unpredictable. Moreover, in the overall process of the present invention, the hydrogen iodide by-product is available to be recycled, thereby enhancing the economics of the reaction.

The invention has been described in detail with particular reference to preferred embodiments thereof, but it will be understood that variations and modification can be effected within the spirit and scope of the invention.

We claim:

1. A process for the preparation of aromatic dicarboxylic acids which comprises reacting an aromatic diiodide having about 5 to about 20 atoms in the ring or rings thereof, with carbon monoxide in the presence of a soluble homogeneous rhodium catablyst in a reaction medium selected from acetic acid, butyric acid and propionic acid.

2. The process of claim 1 wherein said aromatic diiodides is a toluene diiodide, benzene diiodide, naphthalene diiodide, pyridine diiodide, thiophene diiodide, or pyrrole diiodide.

3. The process of claim 2 wherein the reaction temperature is about 50° to 150° C.

4. A process for the preparation of aromatic organic acid compounds which comprises reacting an aromatic iodide of the formula

I—R—I wherein R represents a substituted or unsubstituted group derived from toluene, benzene, naphthalene, pyridine. thiophene, or pyrrole,
with carbon monoxide in the presence of a soluble homogeneous rhodium catalyst in a reaction medium selected from acetic acid, butyric acid and propionic acid.

5. The process of claim 4 wherein R represents a group derived from benzene or naphthylene.

6. The process of claim 5 wherein the reaction temperature is about 80° to 130° C.

7. The process of claim 6 wherein said reaction medium is acetic acid.

8. The process of claim 7 wherein said R is benzene.

* * * * *